US005736345A

United States Patent [19]
Mather et al.

[11] Patent Number: 5,736,345
[45] Date of Patent: Apr. 7, 1998

[54] ASSAY FOR GROWTH PROMOTING FACTORS UTILIZING MAMMALIAN LUNG CELL LINES

[75] Inventors: Jennie P. Mather; Penelope E. Roberts, both of Millbrae, Calif.

[73] Assignee: Genentech, Inc., South San Francisco, Calif.

[21] Appl. No.: 455,755

[22] Filed: May 31, 1995

Related U.S. Application Data

[60] Division of Ser. No. 910,260, filed as PCT/US91/00878, Feb. 8, 1991, which is a continuation-in-part of Ser. No. 479,130, Feb. 9, 1990, abandoned.

[51] Int. Cl.$^6$ ............... C12N 15/01; C12Q 1/68; G01N 33/483
[52] U.S. Cl. ............... 435/7.21; 435/6; 435/29; 435/405; 435/408
[58] Field of Search ............... 435/6, 7.21, 240.1, 435/240.2, 240.31, 405, 408, 384, 391, 29; 530/399, 350, 398

[56] References Cited

U.S. PATENT DOCUMENTS

| | | |
|---|---|---|
| 4,885,238 | 12/1989 | Reddel et al. |
| 4,889,808 | 12/1989 | Rappaport |
| 5,089,397 | 2/1992 | Kushner et al. |
| 5,356,806 | 10/1994 | Harris et al. |
| 5,364,785 | 11/1994 | Mather et al. |

FOREIGN PATENT DOCUMENTS

| | | |
|---|---|---|
| 0082974 | 7/1983 | European Pat. Off. |
| WO89/03994 | 5/1989 | WIPO |

OTHER PUBLICATIONS

Baserga, R.; In: Cell growth and division. Baserga, R. editor. Chapter 1. IRL Press, Oxford, UK, 1989.
Greenwood, D, et al; In: Cell growth and division. Baserga, R. editor. Chapter 1. IRL Press, Oxford, UK, 1989.
Patton, et al. Experimental Lung Research 11:277–294, 1986.
Klann et al., "Effects of Retinoic Acid on Cell Proliferation and Cell Differentiation in a Rat Tracheal Epithelial Cell Line" *Cell Tissue Kinet* 15:473–482 (1982).
Cascieri et al., "Inability of a Mouse Cell Line Transformed to Produce Biologically Active Recombinant Human Insulin–Like Growth Factor I (IGF–I) to Respond to Exogenously Added IFG–I", *Endocrinology* 122(4):1314–1320 (1988).
Celis et al., "Computerized, Comprehensive Databases of Cellular and Secreted Proteins From Normal Human Embryonic Lung MRC–5 Fibroblasts: Identification of Transformation and/or Proliferation Sensitive Proteins", *Electrophoresis* 10:76–115 (1989).
Chopra et al., "Propagation of Differentiating Normal Human Tracheobronchial Epithelial Cells in Serum–Free Medium" *Journal of Cellular Physiology* 130:173–181 (1987).

Evans et al., "Lung Cell Kinetics" *Lung Cell Biology* pp. 1–89 (1989).
Frehney, "Culture of Specific Cell Types" *Culture of Animal Cells A Manual of Basic Technique* pp. 267–268 (1987).
Honegger et al., "Insulin–like Growth Factors I and II in Fetal and Adult Bovine Serum" *Journal of Biological Chemistry* 261(2):569–574 (1986).
Jones et al., "Benzo(a)pyrene Hydoxylase Activity in Enriched Populations of Clara Cells and Alveolar Type II Cells From Control and β–Napthoflavone–pretreated Rats" *Cancer Research* 42:4658–4663 (1982).
Lechner et al., "Clonal Growth of Normal Adult Human Bronchial Epithelial Cells at Clonal Density" *Journal of Tissue Culture Methods* 9 (2):43–48 (1985).
Lechner et al., "A Serum–free Method for Culturing Normal Human Bronchial Epithelial Cells at Clonal Density" *Journal of Tissue Culture Methods* 9(2) 43–48 (1985).
Lee et al., "Growth and Differentiation of Hamster Tracheal Epithelial Cells in Culture" *Experimental Lung Research* 6:27–45 (1984).
Loo et al., "Extended Culture of Mouse Embryo Cells Without Senescence: Inhibition of Serum" *Science* 236:200–202 (Apr. 10, 1987).
Mass et al., "The Effect of 12–O–Tetradecanoylphorbol–13–acetate and other Tumor Promoters on the Colony of Formation of Rat Tracheal Epithelial Cells in Culture" *Carcinogenesis* 5 (12):1597–1601 (1984).
Massaro, "Nonciliated Bronchiolar Epitelial (Clara) Cells" *Lung Cell Biology* pp. 81–114 (1989).
Massaro et al., "Development of Bronchiolar Epithelium in Rats" *American Journal of Physiology* 250 (5):783–788 (1986).
Mather et al., "Hormones and Growth Factors in Cell Cultures: Problems and Perspectives" *Cell, Tissue and Organ Cultures in Neurobiology,* Federoff & Hertz pp. 621–630 (1977).
Netter, "Ultrastructure of Tracheal Bronchial and Bronchiolar Epithelium" *The CIBA Collection of Medical Illustrations* 7:26 (1979).

(List continued on next page.)

Primary Examiner—Christina Chan
Assistant Examiner—F. Pierce VanderVegt
Attorney, Agent, or Firm—Wendy M. Lee; Deidre L. Conley

[57] ABSTRACT

A novel bronchial or bronchiolar epithelial cell from normal neonatal mammalian lung has been isolated, established and maintained for multiple passages in the absence of serum, without undergoing crisis or senescence. By careful manipulation of the nutritional/hormonal microenvironment we have been able to select, from a heterogeneous population, a single epithelial cell type which can maintain highly differentiated features in vitro. This cell type has characteristics of bronchiolar epithelial cells. A clonal line, RL–65, has been selected and observed for more than 3 years in continuous culture. It has been characterized by ultrastructural, morphological and biochemical criteria.

11 Claims, 8 Drawing Sheets

OTHER PUBLICATIONS

Piltch et al., "A Cloned Rat Thymic Epithelial Cell Line Established From Serum–Free Selective Culture" *In Vitro Cellular & Developmental Biology* 24 (4) :289–293 (1988).

Plopper et al., "Ultrastrucure of the Nonciliated Bronchiolar Epithelial (Clara) cell of Mammalian Lung: I. A Comparison of Rabbit, Guinea Pig, Rat, Hamster, and Mouse" *Experimental Lung Research* 1:139–154 (1980).

Roberts et al., "A Novel Epithelial Cell From Neonatal Rat Lung: Isolation and Differentiated Phenotype" *Properties of Lung Epithelial Cells* pp. L415–L425 (1990).

Schumann et al., "Isolation, Characterization, and Long-term Culture of Fetal Bovine Tracheal Epithelial Cells" *In Vitro Cellular & Devopmental Biology* 24 (3):211–216 (1988).

Scopes, "Analysis for Purity; Crystallization" *Protein Purification Principles and Practice*, Springer Advanced Texts in Chemistry p. 248 (1983).

Siegfried, "Detection of Human Lung Epithelial Cell Growth Factors Produced by a Lung Carcinoma Cell Line: Use in Culture of Primary Solid Lung Tumors[1]" *Cancer Research* 47:2903–2910 (Jun. 1, 1987).

Siegfried et al., "Cytotoxicity of chemical Carcinogens Towards Human Bronchial Epithelial Cells Evaluated in a Clonal Assay" *Carcinogenesis* 5(10):1317–1322 (1984).

Singh et al., "A Quantitative Assay for a Clara Cell–Specific Protein and Its Application in the Study of Development of Pulmonary Airways in the Rat" *Pediatric Research* 20 (8):802–805 (1986).

Thomassen et al., "Clonal Proliferation of Rat Tracheal Epithelial Cells in Serum–free Medium and Thier Responses to Hormones, Growth Factors and Carcinogens" *Carcinogenesis* 7(12):2033–2039 (1986).

Tsao et al., "Clonal growth of normal human epidermal keratinocytes in a defined medium" *J. Cellular Physiology* 110:219–229 (1982).

Willey et al., "Bombesin and the C–Terminal Tetradecapeptide of Gastrin–releasing Peptide are Growth Factors for Normal Human Bronchial Epithelial Cells" *Exp. Cell Res.* 153:245–248 (1984).

Wu et al., "Continuous Multiplication of Rabbit Tracheal Epithelial Cells in a Defined Hormone–Supplemented Medium" *In Vitro* 18(9):800–812 (1982).

Wu et al., "Effects of Retinoids on Human Bronchial Epithelial Cells: Differential Regulation of Hyaluronate Synthesis and Keratin Protein Synthesis" *J. Cellular Physiology* 127:73–82 (1986).

Wu et al., "Expression of Tracheal Differentiated Functions in Serum–free Hormone Supplemented Medium" *J. Cellular Physiology* 125:167–181 (1985).

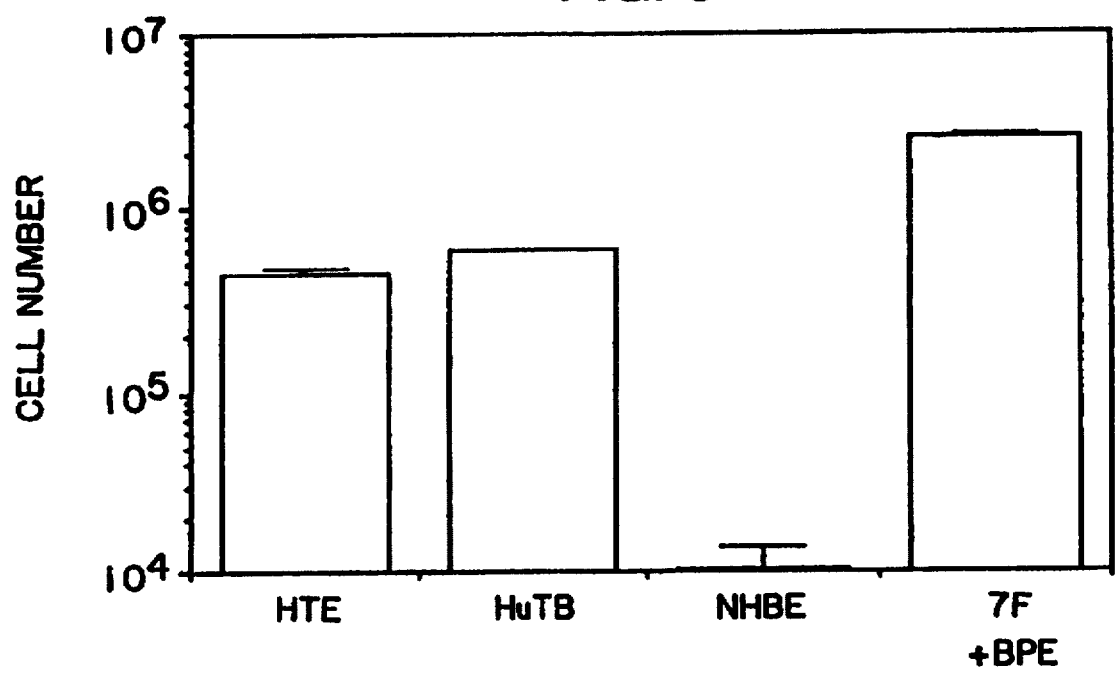

RL-65

Rat
Bronchiole

Mouse Clara

```
              ALUI
              SSTI                               TAQI
              SACI                               SALI
              HGIJII                             HINDII
              HGIAI                              HINCII
              BSP1286                            PLEI    ALUI
              BANII                              HINFI   PVUII
              TAQI                      RMAI ACCI NSPBII
    1   TTCGAGCTCG CCCGACATTG ATTATTGACT AGAGTCGACA GCTGTGGAAT
        AAGCTCGAGC GGGCTGTAAC TAATAACTGA TCTCAGCTGT CGACACCTTA

NLAIV
                              SCRFI
                              ECORII
                              BSTNI
                              BSAJI
   51   GTGTGTCAGT TAGGGTGTGG AAAGTCCCCA GGCTCCCCAG CAGGCAGAAG
        CACACAGTCA ATCCCACACC TTTCAGGGGT CCGAGGGGTC GTCCGTCTTC

NSII
              AVAIII                                     NLAIV
              NLAIII                                     SCRFI
              SPHI                  SCRFI                ECORII
              NSPI SFANI            ECORII               BSTNI
              NSPHI                 BSTNI                BSAJI
  101   TATGCAAAGC ATGCATCTCA ATTAGTCAGC AACCAGGTGT GGAAAGTCCC CAGGCTCCCC
        ATACGTTTCG TACGTAGAGT TAATCAGTCG TTGGTCCACA CCTTTCAGGG GTCCGAGGGG

SFANI
                        NSII
                        AVAIII
                        NLAIII
                        SPHI
                        NSPI
                        NSPHI
  161   AGCAGGCAGA AGTATGCAAA GCATGCATCT CAATTAGTCA
        TCGTCCGTCT TCATACGTTT CGTACGTAGA GTTAATCAGT

BSRI
                ACII           ACII FOKI ACII        ACII            ACII
  201   GCAACCATAG TCCCGCCCCT AACTCCGCCC ATCCCGCCCC TAACTCCGCC CAGTTCCGCC
        CGTTGGTATC AGGGCGGGGA TTGAGGCGGG TAGGGCGGGG ATTGAGGCGG GTCAAGGCGG
```

FIG. 7A

```
                NLAIII
                STYI
                NCOI
                DSAI
        ACII    BSAJI
    261 CATTCTCCGC CCCATGGCTG ACTAATTTTT TTTATTTATG
        GTAAGAGGCG GGGTACCGAC TGATTAAAAA AAATAAATAC

MNLI
              FNU4HI
              SFII BSAJI
        BSAJI BGLI        DDEI
        HAEIII HAEIII     MNLI                        MNLI
        MNLI  MNLI ACII  HAEIII    ALUI               MNLI
    301 CAGAGGCCGA GGCCGCCTCG GCCTCTGAGC TATTCCAGAA GTAGTGAGGA GGCTTTTTTG
        GTCTCCGGCT CCGGCGGAGC CGGAGACTCG ATAAGGTCTT CATCACTCCT CCGAAAAAAC

SCRFI
                                           NCII
        STYI                               MSPI
        BSAJI                              HPAII
        AVRII                              CAUII
        HAEIII                             HAEIII
        STUI                               SAU96I
        HAEI              ALUI    ASUI
        MNLI RMAI         HINDIII
    371 GAGGCCTAGG CTTTTGCAAA AAGCTTATCG GGCCGGGAAC
        CTCCGGATCC GAAAACGTTT TTCGAATAGC CCGGCCCTTG

TFII
              HINFI
              ACII
              THAI
              FNUDII                  MAEII     ACII
              BSTUI                   MAEIII    RSAI
    401 GGTGCATTGG AACGCGGATT CCCCGTGCCA AGAGTGACGT AAGTACCGCC
        CCACGTAACC TTGCGCCTAA GGGGCACGGT TCTCACTGCA TTCATGGCGG
```

FIG. 7B

```
                                                      FNU4HI
                          BSTXI                       ACII
                          SAU96I                      THAI
         PLEI             HAEIII    STYI              FNUDII
         HINFI            ASUI      BSAJI             BSTUI        ASEI
                                            SP6 PROMOTER
   451   TATAGAGTCT   ATAGGCCCAC   CCCCTTGGCT   TCGTTAGAAC   GCGGCTACAA
         ATATCTCAGA   TATCCGGGTG   GGGGAACCGA   AGCAATCTTG   CGCCGATGTT

MAEIII
         MSEI                                         HPHI
                           NOTE ATG
   501   TTAATACATA   ACCTTATGTA   TCATACACAT   ACGATTTAGG   TGACACTATA
         AATTATGTAT   TGGAATACAT   AGTATGTGTA   TGCTAAATCC   ACTGTGATAT

SAU96I
                                                                AVAII
                                                                ASUI
                                                                SCRFI
                                                                ECORII
                                                                BSTNI
         FOKI                                                   BSAJI
         SP6 RNA START
   551   GAATAACATC   CACTTTGCCT   TTCTCTCCAC   AGGTGTCCAC   TCCCAGGTCC
         CTTATTGTAG   GTGAAACGGA   AAGAGAGGTG   TCCACAGGTG   AGGGTCCAGG

BSPMI
                              ALUI        PSTI
              MNLI            HINDIII     FNU4HI
              BSAJI    DDEI               BBVI
              CLONING LINKER
   601   AACTGCACCT   CGGTTCTAAG   CTTGGGCTGC   AGGTCGCCGT
         TTGACGTGGA   GCCAAGATTC   GAACCCGACG   TCCAGCGGCA

MSEI    HGAI         BSMI
   641   GAATTTAAGG   GACGCTGTGA   AGCA
         CTTAAATTCC   CTGCGACACT   TCGT
```

FIG. 7C

ASSAY FOR GROWTH PROMOTING FACTORS UTILIZING MAMMALIAN LUNG CELL LINES

CROSS REFERENCE

This application is a divisional of co-pending U.S. application Ser. No. 07/910,260 filed 16 Jul. 1992, which is a 371 of PCT/US91/00878, filed 8 Feb. 1991, which application is a continuation-in-part of U.S. application Ser. No. 07/479,130 filed 9 Feb. 1990, now abandoned which applications are incorporated herein by reference and to which applications priority is claimed under 35 USC §120.

FIELD OF THE INVENTION

This invention relates generally to a method of isolating a normal mammalian bronchial or bronchiolar epithelial lung cell; to the isolated mammalian epithelial lung cells produced by the method; to the use of the isolated mammalian epithelial lung cell for the production of proteins and as an assay system for pituitary factors which promote the growth of such mammalian epithelial lung cells. The unique method of isolating the lung cells results in novel bronchial or bronchiolar epithelial cells isolated from mammalian lung which grow in serum-free defined medium and which exhibit accelerated growth in the presence of mammalian pituitary extract.

BACKGROUND AND PRIOR ART

The lung is a complex organ composed of over 40 different cell types. Work on small cell carcinoma and recent advances in endocrinology have led to the recognition that the lung is the site of production of, and target tissue for a number of endocrine, paracrine and autocrine factors. While several tissue culture systems have been reported for primary culture of cells from the lung, specifically tracheobronchial epithelium (Chopra et. al., J. Cell Physiol. 130:173-181 [1987]; Lechner et al., In Vitro 18:633-642 [1982]; Lee et al., Exp. Lung Res. 6:27-45 [1984]; Schumann et al., In Vitro 24:211-216 [1988]; and Wu et. al., In Vitro 18:800-812 [1982]), epithelial cell lines which can maintain their differentiated function in vitro have been difficult to establish without viral or chemical transformation or immortalization by transfection with various oncogenes. Reddel et. al., PCT 89/03994 disclose human bronchial epithelial cells after vital transformation capable of growth in culture. These cells were transformed with SV40 or adenovirus-12 SV40 hybrid virus or with a recombinant plasmid containing portions of the Rous sarcoma virus. Clearly these cells are not the same as the normal cells of the present invention which do not contain such a transforming virus. There was a need for a method of isolating mammalian bronchial epithelial cell without transformation with a virus or other genetic vector altering the genetic composition and phenotype of the cell. Moreover, there was a need for specific media conditions needed for the isolation and for the growth of non-vitally transformed bronchial epithelium.

Serum is known to support the growth of many cell types, however it is complex and not well defined. In vivo, a cell is normally exposed to the equivalent of serum only under special circumstances involving tissue injury and blood coagulation. In vitro, serum may not support the growth of some cell types, due to specific inhibition or a failure to provide an adequate concentration of stimulatory factors. Mather and Sato demonstrated that a serum-free hormonally defined medium for melanoma cells could be used to select for that same cell type when used as the culture media for a mixed cell population (Mather, J. P. and Sato, G., Hormones and Growth Factors in Cell Cultures: problems and perspectives. In Cell Tissue and Organ Cultures in Neurobiology, New York: Academic Press, pp. 619–630 [1978]). Piltch et al were able to select for differentiated epithelial cells from rat thymus, and maintain these cells continuously in a defined serum-free medium supplemented with hormones (Piltch et al., In Vitro 24:289–293 [1988]). Loo and co-workers have described a serum-free, hormonally defined culture system for the establishment of a mouse embryo cell, selected from whole embryos. These cultures, when carried in the presence of serum, undergo a well-defined crisis or senescence (Loo et al., Science 236:200–202 [1987]). This senescence does not occur when these cultures are carried continuously in serum-free, hormonally defined culture. Therefore, there was a need for a culture procedure utilizing hormone-supplemented, serum-free medium as a method of the selection of specific cell types from the lung.

SUMMARY OF THE INVENTION

A novel bronchial or bronchiolar epithelial cell from normal neonatal rat lung has been isolated, established and maintained for multiple passages in the absence of serum, without undergoing crises or senescence. By careful manipulation of the nutritional/hormonal microenvironment we are able to reproducibly select, from a heterogeneous population, a single epithelial cell type which can maintain highly differentiated features in vitro. This cell type has characteristics of a mammalian bronchial or bronchiolar epithelial cells. A clonal line, RL-65, has been selected and observed for more than 2 years in continuous culture. It has been characterized by ultrastructural, morphological and biochemical criteria. The strategy used for isolation and eventual establishment of cell lines from normal lung tissue is unique in that it utilizes a completely defined medium (in the absence of serum) to initially select for a specific type from the time of explant. The cells produced by the method of the present invention, non-transformed epithelial cell lines from normal mammalian lung tissue, may be used to assay the activity of both naturally occurring and synthetic molecules that regulate lung endocrinology and physiology. These non-transformed epithelial lung cells may be used in the production of proteins and as an assay cell line responding to growth promoting factors thereby enabling the isolation of such growth promoting factors.

Definitions
  BPE: Bovine Pituitary Extract
  FBS: Fetal Bovine Serum
  FGF: Fibroblast Growth Factor
  $FGF_a$: Fibroblast Growth Factor-a
  FSH: Follicle Stimulating Hormone
  TSH: Thyroid Stimulating Hormone
  HLH: Human Leutenizing Hormone
  ACTH: Adrenocorticotropic Hormone
  OXY: Ocytocin
  ADH: Vasopressin
  αMSH: α Melanocyte Stimulating Hormone
  βMSH: β Melanocyte Stimulating Hormone
  hPRL: Human Prolactin

DESCRIPTION OF THE FIGURES

FIG. 5 Growth of RL-65 in various basal media formulations supplemented with hormones and growth factors.

FIG. 7A–C. The complete nucleotide sequence of pSVI (SEQ ID NO:1).

DESCRIPTION OF THE PREFERRED EMBODIMENTS

Figure 1A:
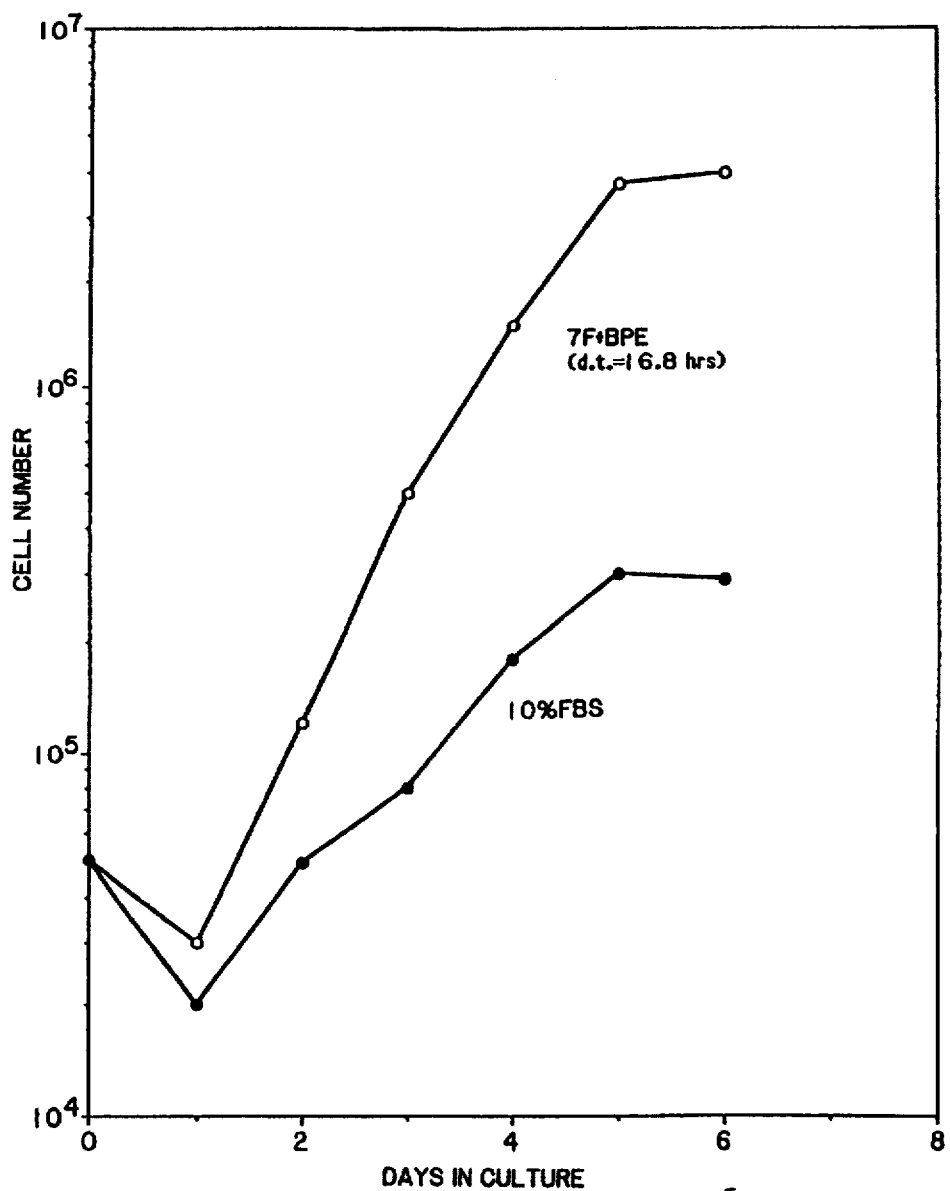
FIG. 1–B. A. Growth of RL-65 in 7F+BPE vs 10% FBS. Cells were plated at $5 \times 10^4$ cells/21 $cm^2$ and counted on day 5. B. Thymidine incorporation 72 hrs. after plating (see Methods for definitions).

The lungs have multiple functions, but they have been difficult to study in vitro, largely because of the many diverse cell types. It was important to ascertain whether or not novel epithelial cell types of the lung could be isolated and established in vitro by careful manipulation of the nutritional/hormonal culture environment. We report here a serum-free, hormone-supplemented culture system which will initially select for a single epithelial cell type from normal, neo-natal mammalian (rat) lung. These cells will undergo multiple passages without crisis or senescence. A clonal cell line established in this fashion has been designated RL-65 and its properties are described below.

The distribution and frequency of ten morphologically distinct cell types has been described in the surface epithelium of the rat intrapulmonary airways (Evans and Shami, Lung cell kinetics, In: Lung Cell Biology, D. Massaro, ed., New York, N.Y.: Marcel Dekker, pp 1–89 [1989]). Eight of these cell types are epithelial, differentiating into secretory cells, cilliated cells, and cells whose main recognized function is to provide a large surface area for gas exchange. The maturation of the alveolar type 2 cell and the surfactant system is achieved prenatally, while maturation of the epithelium of the respiratory bronchioles and the small conducting airways occurs just after birth just prior to restructuring of the lung parenchyma and alveolarization (day 4–13) (Burri, P. H., Anat. Rec. 180:77–98 [1974]; Massam and Massam, Am. J. Physiol. 250:R783–R788 [1986b]).

The RL-65 cell line, derived from the lungs of 5 day old rats, has phenotypic characteristics typical for cells of the airway epithelium. Studies are currently underway to further define the specific origin of this cell type. Evidence suggests it may be a type of progenitor cell with the capacity to differentiate along several pathways, depending on alterations in the cell culture microenvironment. This cell type is not readily observed during the first week in culture, but can easily be identified after 12 to 14 days in serum-free defined medium supplemented with 11F (see Table 1). This may be due to a change in morphology after time in culture, or its appearance may be facilitated by the death of most of the other cell types in the heterogeneous population. Alternatively, the late appearance of this cell type may be due to continued differentiation in vitro. Growth control and differentiation may be regulated by changes in culture conditions. The careful and timely addition/deletion of such components as BPE or retinoic acid, for example, may result in a culture condition in which cells either become committed to squamous differentiation and cornification, or further cell division.

TABLE 1

| Factor | 7F | 11F |
|---|---|---|
| Insulin (porcine) | 1 μg/ml | 10 μg/ml |
| Transferrin (human) | 10 μg/ml | 10 μg/ml |
| Epidermal Growth Factor | — | 5 ng/ml |
| Ethanolamine | $1 \times 10^{-4}$M | $1 \times 10^{-6}$M |
| Phosphoethanolamine | $1 \times 10^{-4}$M | $1 \times 10^{-6}$M |
| Selenium | $2.5 \times 10^{-8}$M | $2.5 \times 10^{-8}$M |
| Hydrocortisone | $2.5 \times 10^{-7}$M | $1 \times 10^{-9}$M |
| Forskolin | 5 μM | 1 μM |
| Progesterone | — | $1 \times 10^{-8}$M |
| Triiodothyronine | — | $5 \times 10^{-12}$M |
| Bovine lipoprotein | — | 0.5% |

Bovine pituitary extract (BPE) used at a concentration of 150 μg protein/ml medium.
Retinoic acid (0.05 μM) + BPE is optimal for growth in 7F.

The RL-65 cells have a phenotype distinct from that reported for other types of long term cultures of lung cells, and other established lung cell lines. Bombesin, the gastrin releasing peptide found in neuroendocrine cells of the lung, was not produced in the RL-65. This suggests that they are probably not of neuroendocrine origin. The proteolytic activity of the RL-65, as well as PGE2 production, points toward an important role in the detoxification of reactive compounds in the lung. This is further supported by the fact that this cell type has a large number of acetylated LDL receptors, perhaps for the purpose of scavenging and degrading extracellular molecules. It therefore may possess a "scavenger cell" pathway of acetylated LDL metabolism similar to that found in macrophages, endothelial cells and microgila (Garrels, J. I., J. Biol. Chem. 254:7961–7966 [1979]; Garrels et al., in Two Dimensional Gel Electrophoresis of Proteins: Methods and Applications, Cells & Bravo, ed., New York: Academic Press p. 38 [1984]; Githens et al., In Vitro 25(8):697–698 [1989]; and Schumann et al., In Vitro 24:211–216 [1988]).

The method of the present invention results in the production of novel mammalian epithelial lung cell lines. This method may be used to isolate such cells from the lung of any mammal, for example rat, human, rabbit, cow, and sheep. The method first incubates the mechanically and/or enzymatically isolated fragments of lung tissue in serum free 11F medium for a period of from 10 to 90 days or more, more preferably, 15 to 50 days, and most preferably 21 to 35 days. The 11F medium is changed about every three days. This initial incubation is selective for the preferential survival of the epithelial lung cells of the present invention.

Following the initial incubation in 11F medium, the cultured lung cells are moved to medium containing pituitary extract (PE) or PE is added to the medium. The pituitary extract may be present in an amount from 5 to 900 μg/ml, more preferably 50 to 300 μg/ml, and most preferably 100 to 500 μg/ml. The optimized basal medium (7F) for this cell line, RL-65, is Hams F12/DME plus insulin (1 μg/ml), human transferrin (10 μg/ml), ethanolamine (10$^{-4}$M), phosphoethanolamine (10$^{-4}$M), selenium (2.5×10$^{-8}$M), hydrocortisone (2.5×10$^{-7}$M), and forskolin (5 μM). The addition of 150 μg/ml of bovine pituitary extract (BPE) to the defined basal medium stimulates a 5–20 fold increase in cell number, and a 10–100 fold increase in thymidine incorporation. The addition of retinoic acid results in further enhancement of cell growth and complete inhibition of keratinization. The 11F media will support growth of all such bronchial epithelial lung cells, however optimized medium for similar cells isolated from different species may differ in the optimal concentration of each component of the media, and in the ratios of components in the media. The optimization of each component for a specific cell is readily accomplished by varying the concentration of each component while keeping the other components constant and selecting for the optimum phenotype desired.

The lung cells produced by the methods of the present invention may be grown in pituitary extract as described in Example 3. This extract may be made from any mammalian pituitary, including cow, human, rat, sheep, goat, horse, rabbit and pig.

In the presence of pituitary extract, the addition of retinoic acid further promotes the growth of the lung cells of the present invention. The concentration of retinoic acid may be between 0.0001 and 10 μmolar more preferably between 0.01 and 1 μmolar, and most preferably between 0.03 and 0.10 μmolar.

Deposit of Cell Line RL-65

The following strain has been deposited with the American Type Culture Collection, 12301 Parklawn Drive, Rockville, Md., U.S.A. (ATCC):

| Strain | ATCC Accession No. | Deposit Date |
| --- | --- | --- |
| RL-65 | CRL 10354 | February 9, 1990 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The organisms will be made available by ATCC under the terms of the Budapest Treaty, and subject to an agreement between Genentech, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC 122 and the Commissioners rules pursuant thereto (including 37 CFR 1.14 with particular reference to 886 OG 638).

The assignee of the present application has agreed that if the cultures on deposit should die or be lost or destroyed when cultivated under suitable conditions, they will be promptly replaced on notification with a viable specimen of the same culture. Availability of the deposited cultures is not to be construed as a license to practice the invention in contravention of the rights granted under the authority of any government in accordance with its patent laws.

Isolation Procedure

We have demonstrated that, because each cell type, even within the same region of the same lung tissue requires a different combination or concentration of nutrients, hormones and/or growth factors, a carefully tailored serum-free environment will lead to the isolation and identification of new type of bronchial epithelial cell from the lung which have not previously been established in vitro. The isolation method of the present invention provides the opportunity to isolate and characterize these bronchial epithelial cells. The bronchial epithelial lung cells may be isolated from any animal, preferably a mammal, such as bovine, ovine, canine, feline, primate and rodent. Among the preferred mammals are: cow, human, rat, mouse, guinea pig, sheep, goat, horse, rabbit and pig. The epithelial lung cell of the present invention is exemplified by RL-65. The unique gene products of these bronchial epithelial cells further define the phenotype of these lung cells.

Materials and Methods

Animals 5 day old male Sprague Dawley rats used for these experiments were obtained from Simonsen Labs, Gilroy, Calif..

Materials.

Dulbecco's Modified Eagle's Medium, high glucose (DME), and Ham's F12 medium (F12) were obtained in powder form from Grand Island Biological Co.(GIBCO), Grand Island, N.Y.; porcine insulin (pins), human transferrin (hTF), hydrocortisone (HC), progesterone (P), ethanolamine (Eth), phosphoethanolamine (PEth), triiodothyronine (T3), and soybean trypsin inhibitor (STI), were obtained from Sigma Chemical Co., St. Louis, Mo.; trypsin (0.05%+0.0.53 mm EDTA) was obtained from GIBCO; epidermal growth factor (EGF) from Collaborative Research, Waltham, Mass.; forskolin (FK) was obtained from Calbiochem, La Jolla, Calif.; bovine lipoprotein (predominantly HDL) (Excyte®) was obtained from Miles Laboratories, Napierville, Ill.; sodium selenite (Sel) from Johnson Matthey Inc. (Aesar, Seabrook, N.H.); whole mixed sex bovine pituitaries were obtained from Pel Freeze, Rogers, Ark.; human plasma fibronectin (fbn) was obtained from Bethesda Research Labs (GIBCO), Bethesda, Md.; tubulin, desrain and vimentin MAB's were obtained from Chemicon International, Los Angeles, Calif.; rabbit antihuman keratin and rabbit antichicken actin were obtained from Polysciences, Warrington Pa.; fluorescein isothiocyanate (FITC) conjugated, F(ab1)2 fragments of goat antimouse and antirabbit IgG (H and L chains specific) were obtained from Jackson ImmunoResearch Laboratories, West Grove, Pa. DiI-Ac-LDL was obtained from Biomedical Technologies, Stoughton, Mass. The following pituitary factors were obtained from Sigma Chemical Co.: Growth hormone (gh), follicle stimulating hormone (FSH), thyroid stimulating hormone (TSH), human luteinizing hormone (hLH), human prolactin (hPRL), adrenocortocotropic hormone (ACTH), oxytocin (OXY), vasopressin (ADH), a and β melanocyte stimulating hormone (a, b, MSH), βlipotropin fragments (βlipo), a, b, g endorphin (END). Fibroblast growth factor (FGF) was obtained from Collaborative Research. Two-dimensional gels were run and computer analyzed by Protein Databases Inc. (Huntington Station, N.Y.). Radiochemicals were purchased from New England Nuclear (Boston, Mass.). Recombinant human TGFβ was supplied by Genentech.

Culture Media and Conditions

DME and Ham's F12 (1:1 w/w) were dissolved in Milli-Q water, and supplemented with 1.2 g/L NaHCO3, 0.4 g/L glutamine and 15 mM Hepes. Hormones, trace elements, vitamins and phospholipids used to supplement the serum-free medium are shown in Table 1. All of these factors are prepared as sterile stock solutions at 100–1000 fold final concentration and added to the medium just prior to use. Bovine pituitary extract (BPE) was prepared by the method of Tsao et al (J. Cell Physiol. 110:219–229 [1982]). Cells were incubated in a 5% $CO_2$/95% air, $H_2O$ saturated atmosphere at 37° C.

Expression of Recombinant Proteins in Lung Cells

The lung cells of the present invention, such as the RL-65, may be used in the production of proteins. The production of recombinant proteins may be achieved by first inserting a DNA sequence encoding a desired protein and capable of expression into the lung cells of the present invention. Secondly, the lung cells of the present invention, may be used to synthesize the proteins they encode, preferentially those proteins which are normally secreted, thereby facilitating their detection, purification and use.

For recombinant synthesis, it is first necessary to secure nucleic acid that encodes a desired protein product. DNA encoding a desired protein may be obtained from a source of cells for the product by (a) preparing a cDNA library from these cells, (b) conducting hybridization analysis with labeled DNA encoding the desired protein or fragments thereof (up to or more than 100 base pairs in length) to detect clones in the library containing homologous sequences, and (c) analyzing the clones by restriction enzyme analysis and nucleic acid sequencing to identify full-length clones. DNA that is capable of hybridizing to the DNA encoding the desired protein under low stringency conditions is useful for identifying DNA encoding the desired product. Both high and low stringency conditions are defined further below. Alternatively, genomic libraries will provide the desired DNA. Once the DNA encoding the desired protein has been identified and isolated from the library it is ligated into a replicable vector for further cloning or for expression.

It is preferable to use the DNA encoding the desired protein to transform host cells capable of accomplishing protein processing so as to obtain the protein in the culture medium, i.e., obtain a secreted molecule.

Useful Vectors

The vectors and methods disclosed herein are suitable for use in host lung cells for the production of a wide range of proteins in general, expression vectors containing control sequences that are derived from species compatible with the host lung cell are used. For use in mammalian cells, the control functions on the expression vectors are often provided by viral material. For example, commonly used promoters are derived from the genomes of polyoma, Adenovirus 2, retroviruses, cytomegalovirus, and most frequently Simian Virus 40 (SV40). Other promoters are those from heterologous sources, e.g., the beta actin promoter. The early and late promoters of SV40 virus are particularly useful because both are obtained easily from the virus as a fragment that also contains the SV40 viral origin of replication [Fiers et al., Nature, 273:113 (1978)]. Smaller or larger SV40 fragments may also be used, provided there is included the approximately 250-bp sequence extending from the HindIII site toward the Bg/1 site located in the viral origin of replication. The immediate early promoter of the human cytomegalovirus is conveniently obtained as a HindIII restriction fragment. Greenaway et al., Gene, 18:355-360 (1982). Further, it is also possible, and often desirable, to utilize promoter or control sequences normally associated with the desired gene sequence, provided such control sequences are compatible with the host cell systems.

Transcription of a DNA encoding the desired protein in lung cells is increased by inserting an enhancer sequence into the vector. The enhancer is a cis-acting element of DNA, usually about from 10 to 300 bp, that acts on a promoter to enhance its transcription-initiation activity. Enhancers are relatively orientation and position independent, having been found 5' (Laimins et al., Proc. Natl. Acad. Sci. U.S.A., 78:993 [1981]) and 3' (Lusky et al., Mol. Cell Bio., 3:1108 [1983]) to the transcription unit, within an intron (Banerji et al., Cell, 33:729 [1983]) as well as within the coding sequence itself (Osborne et al., Mol. Cell Bio., 4:1293 [1984]). Preferably, however, the enhancer element is located upstream of the promoter sequence for this invention. Many enhancer sequences are now known from mammalian genes (globin, elastase, albumin, a-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. Most preferred herein is the SV40 enhancer region.

Expression vectors used in host lung cells will also contain polyadenylation sites. Examples of polyadenylation regions are those derived from viruses such as, e.g., the SV40 (early and late) or HBV.

An origin of replication may be provided either by construction of the vector to include an exogenous origin, such as may be derived from SV40 or other vital (e.g., Polyoma, Adeno, VSV, BPV) source, or may be provided by the host cell. If the vector is integrated into the host lung cell chromosome, the latter is often sufficient.

Lung cells containing the vector may be selected by the use of dominant selection, which refers to a selection scheme that does not require the use of a mutant cell line. This method typically employs a drug to arrest growth of a host cell. Those cells that have a novel gene would express a protein conveying drug resistance and would survive the selection. Examples of drugs used in dominant selection include neomycin (Southern and Berg, J. Molec. Appl. Genet., 1:327 [1982]), mycophenolic acid (Mulligan and Berg, Science, 209: 1422 [1980]), or hygromycin (Sugden et al., Mol. Cell. Biol., 5:410–413 [1985]). The three examples given above employ bacterial genes under eukaryotic control to convey resistance to the appropriate drug, i.e., neomycin (G418 or geneticin), xgpt (mycophenolic acid), or hygromycin, respectively.

Satisfactory amounts of protein are produced by cell cultures; however, refinements, using a secondary coding sequence, serve to enhance production levels even further. One secondary coding sequence comprises dihydrofolate reductase (DHFR) that is affected by an externally controlled parameter, such as methotrexate (MTX), thus permitting control of expression by control of the methotrexate concentration. Plasmid pdH135, containing an SV40 promoter and DNA encoding lung surfactant, was shown in Example 4 to be capable of making human lung surfactant C.

Typical Methodology Employable

Construction of suitable vectors containing the desired coding and control sequences employs standard recombinant techniques. Isolated plasmids or DNA fragments are cleaved, tailored, and religated to form the desired plasmid.

If flush ends are required, the cleaved DNA preparation may be treated for 30 minutes at 37° C. with DNA Polymerase I (Klenow fragment) or T4 DNA polymerase, phenol-chloroform extracted, and ethanol precipitated. 3' protruding ends are removed by the 3' to 5' exonucleolytic activity of either enzyme, and the 5' protruding ends are made flush by the 5' to 3' polymerase activity incorporating complementary nt until the end of the fragment is reached.

Size separation of the cleaved fragments may be performed using 6 percent polyacrylamide gel described by Goeddel et al., Nucleic Acids Res., 8:4057 (1980).

For analysis to confirm correct sequences in plasmids constructed, the ligation mixtures are typically used to transform *E. coli* K12 strain 294 (ATCC 31,446) or other suitable *E. coli* strains, and successful transformants selected by ampicillin or tetracycline resistance where appropriate. Plasmids from the transformants are prepared and analyzed by restriction mapping and/or DNA sequencing by the method of Messing et al., Nucleic Acids Res., 9:309 (1981) or by the method of Maxam et. al., Meth. Enzym., 65:499 (1980).

After introduction of the DNA into the lung cell host and selection in medium for stable transfectants, amplification of DHFR-protein-coding sequences is effected by growing host cell cultures in the presence of approximately 200–500 nM concentrations of methotrexate, a competitive inhibitor of DHFR activity. The effective range of concentration is highly dependent, of course, upon the nature of the DHFR gene and the characteristics of the lung cell host. Clearly, generally defined upper and lower limits cannot be ascertained. Suitable concentrations of other folic acid analogs or other compounds that inhibit DHFR could also be used. MTX itself is, however, convenient, readily available, and effective.

Recombinant Methods

In order to simplify the examples and claims, certain frequently occurring methods will be referenced by shorthand phrases.

"Transfection" refers to the taking up of an expression vector by a host cell whether or not any coding sequences are in fact expressed. Numerous methods of transfection are known to the ordinarily skilled artisan, for example, CaPO$_4$ and electroporation. Successful transfection is generally recognized when any indication of the operation of this vector occurs within the host cell.

"Transformation" means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described by Cohen, S. N. Proc. Natl. Acad. Sci. (U.S.A.), 69:2110 (1972); Mandel et al., J. Mol. Biol. 53:154 (1970); and more recently Liljestrom et al., Gene, 40:241–246 (1985), is generally used for prokaryotes or other cells that contain substantial cell-wall barriers. For mammalian lung cells without such cell walls, the calcium phosphate precipitation method of Graham, F. and van der Eb, A., Virology, 52:456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen, P., et al., J. Bact., 130:946 (1977) and Hsiao, C. L., et al., Proc. Natl. Acad. Sci. (U.S.A.) 76:3829 (1979). However, other methods for introducing DNA into cells such as by nuclear injection or by protoplast fusion may also be used.

"Operably linked" refers to juxtaposition such that the normal function of the components can be performed. Thus, a coding sequence "operably linked" to control sequences refers to a configuration wherein the coding sequence can be expressed under the control of these sequences and wherein the DNA sequences being linked are contiguous and, in the case of a secretory leader, contiguous and in reading phase. For example, DNA for a presequence or secretory leader is operably linked to DNA for a polypeptide if it is expressed as a preprotein that participates in the secretion of the polypeptide; a promoter or enhancer is operably linked to a coding sequence if it effects the transcription of the sequence; or a ribosome binding site is operably linked to a coding sequence if it is positioned so as to facilitate translation. Linking is accomplished by ligation at convenient restriction sites. If such sites do not exist, then synthetic oligonucleotide adaptors or linkers are used in accord with conventional practice.

"Control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

"Expression system" refers to DNA sequences containing a desired protein coding sequence and control sequences in operable linkage, so that host lung cells transformed with these sequences are capable of producing the encoded protein. To effect transformation, the expression system may be included on a vector; however, the relevant DNA may then also be integrated into a host chromosome.

As used herein, "cell," "cell line," and "cell culture" are used interchangeably and all such designations include progeny. Thus, "transformants" or "transformed cells" includes the initial transformant and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included. Where distinct designations are intended, it will be clear from the context.

"Digestion" of DNA refers to catalytic cleavage of the DNA with an enzyme that acts only at specific nt sequences in the DNA. Such enzymes are called restriction enzymes, and the sequence for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 µg of plasmid or DNA fragment is used with about 1–2 units of enzyme in about 20 µl of buffer solution. Appropriate buffers and substrate amounts for particular restriction enzymes are specified by the manufacturer. Incubation of about 1 hour at 37° C. is ordinarily used, but may vary in accordance with the suppliers instructions. After incubation, protein is removed by extraction with phenol and chloroform, and the digested nucleic acid is recovered from the aqueous fraction by precipitation with ethanol. When appropriate, digestion with a restriction enzyme is followed by bacterial alkaline phosphatase-mediated hydrolysis of the terminal 5' phosphates to prevent the two ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al., 1982, Molecular Cloning: A Laboratory Manual, New York: Cold Spring Harbor Laboratory, [1982] pp. 133–134).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., Nucleic Acids Res. 9:6103–6114 (1981), and D. Goeddel et al., Nucleic Acids Res. 8:4057 (1980).

"Ligation" refers to the process of forming phosphodiester bonds between two double stranded nucleic acid fragments (T. Maniatis et al., 1982, supra, p. 146). Unless otherwise provided, ligation may be accomplished using known buffers and conditions with 10 units of T4 DNA ligase ("ligase") per 0.5 μg of approximately equimolar amounts of the DNA fragments to be ligated.

"Preparation" of DNA from transformants means isolating plasmid DNA from microbial culture. Unless otherwise provided, the alkaline/SDS method of Maniatis et al., 1982, supra, p. 90, may be used.

"Oligonucleotides" are short-length, single- or double-stranded polydeoxynucleotides that are chemically synthesized by known methods (such as phosphotriester, phosphite, or phosphoramidite chemistry, using solid phase techniques such as described in EP Pat. Pub. No. 266,032 published May 4, 1988, or via deoxynucleoside H-phosphonate intermediates as described by Froehler et al., Nucl. Acids Res., 14:5399–5407 [1986]). They are then purified on polyacrylamide gels.

The foregoing written specification is considered to be sufficient to enable one skilled in the art to practice the invention. The present invention is not to be limited in scope by the culture deposited, since the deposited embodiment is intended as a separate illustration of certain aspects of the invention and any cultures that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

The following examples are intended to illustrate the best mode now known for practicing the invention, but the invention is not to be considered limited thereto.

EXAMPLE 1

ESTABLISHMENT OF LUNG CELL LINE

Primary Culture

Five day old male Sprague Dawley rats were sacrificed by $CO_2$ asphyxiation, the lungs removed, the trachea excised, and the entire lung washed briefly in serum free medium containing 20 mg/ml Gentamycin. The tissue was minced into fragments which were then resuspended in serum-free medium containing 0.05% (w/v) collagenase-dispase and incubated for 30–45 minutes at 37° C. The tissue fragments were washed twice with serum free medium and allowed to settle for 15 minutes after which time the supernatant was removed. The fragments were dispersed by repetitive pipetting in serum-free, hormone supplemented medium (11 F, see Table 1) and aliquoted into fibronectin-coated 60 mm tissue culture dishes. Medium was changed every three days and the cultures maintained in 11F medium for 1 month. At this point bovine pituitary extract (BPE), at 150 μg/ml, was added. Colonies became densely packed monolayers within 7–10 days from the day of addition of BPE, and were passaged at this stage.

Serial Passage

Highly cornified colonies from 60 mm dishes were initially passaged by several trypsinizations (0.05% trypsin-0.53 mM EDTA) for 10' each at 37° C. After neutralization with soybean trypsin inhibitor (STI, 1 mg/ml), cells were washed twice by centrifugation in serum-free F12/DME to remove residual STI, and plated in fibronectin-coated 12-well trays (usually 1 60 mm dish/well) containing 11F supplemented with BPE medium. Cells were subsequently passaged at near-confluency, and seeded into sequentially larger dishes at each passage. Continuous culture was then maintained by passaging at near confluency and at a high seeding density (1:1 or 1:2 split ratio). At no time after the addition of the BPE did the cells undergo a reduction in growth rate or "crisis".

Establishment of a Cloned Lung Epithelial Cell Line.

Lung epithelial cells grown continuously in this way for several months do not require that the dishes be fibronectin coated for attachment. Cloned populations were selected by plating 100–500 cells in a 100 mm dish containing 15% conditioned 11F medium and changing the medium every 3 days. By day 10, colonies were of sufficient size to be cloned by trypsinizing in 6 mm stainless steel cloning rings, (penicylinders, Bellco). Each colony was then seeded into one well of a 24-well tray, grown to near confluency, and the entire well passaged into sequentially larger surface areas at each trypsinization until stock cultures could be maintained in 100 mm dishes. All of the colonies picked had a similar morphology. One of these clones, designated RL-65, was chosen for further characterization, and the optimal nutrient and hormonal requirements were determined. This cell line has been carried in continuous culture for more than 2 years. The RL-65 stocks are currently maintained by passaging every 4–6 days at a 50–200 split ratio.

Growth and Morphology of Primary Cultures.

The initial cell population, which attaches and spreads after plating the dispersed lung tissue, is heterogeneous. By choosing very specific initial culture conditions, followed by a growth medium, we have been able to select against a large number of cell types in the lung as well as allow the survival of the particular cell type we designate as RL-65. If serum is present initially, a heterogeneous culture is obtained and, with time, the culture is eventually overgrown by fibroblastic cell types. If bovine pituitary extract is present initially, even in the absence of serum, a fairly heterogeneous population of non-fibroblastic cells is evident and the population remains heterogeneous with time. The protocol described first uses a serum-free, defined medium (11 F, see table 1) to allow the survival, but not growth of the desired cell type, while not supporting the survival of the majority of cells in the original culture. The selection seems to occur both by providing an environment inadequate for the growth of some cells while actively inhibiting the survival/growth of others. This is followed by the addition of a critical mitogenic component (BPE), and the subsequent optimization of a medium for enhanced growth of the surviving cells. If the optimized medium (7F and BPE) is used in the initial protocol, a diverse population of cells is supported, which may obscure or outstrip the growth of the desired cell type. Thus, in selecting for, and in the establishment of the RL-65 cell, the chronology of events and the timely addition/deletion of the proper supplements is critical.

Continuous Culture.

Figure 1B:
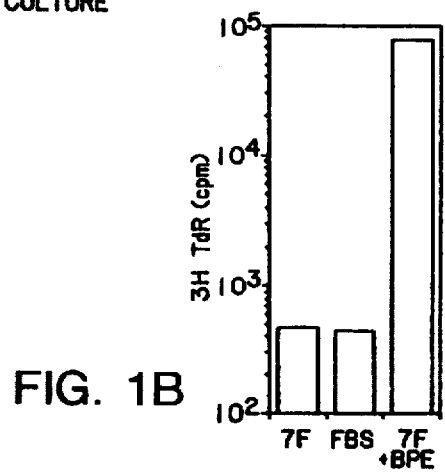
Figure 2:
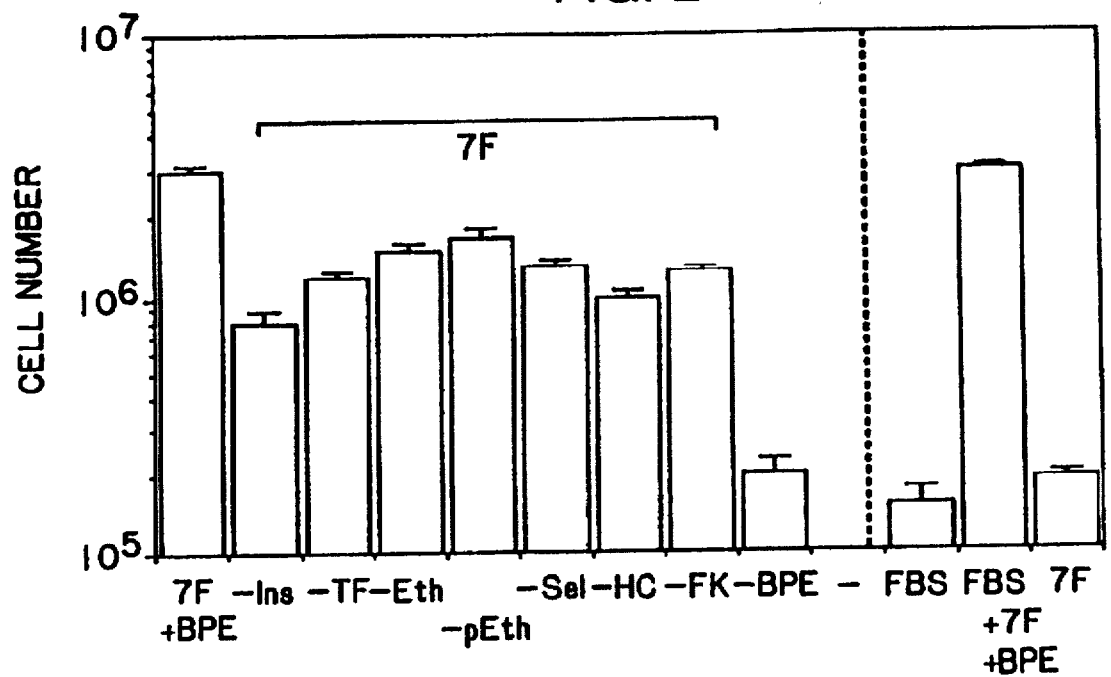
FIG. 2 Effect of FBS, BPE, and individual growth factors in 7F on growth of RL-65. Concentrations are given in Table 1. Each factor and BPE was omitted individually and growth in the remaining components compared with growth in the optimal medium (7F+BPE). Also compared: 10% FBS in presence and absence of 7F+BPE (±-sem).

Long term cultures were established by serially passaging at high density in 15% (v:v) conditioned/fresh 11F medium and BPE, supplemented with fresh 11F and BPE. These cultures became progressively more homogeneous even prior to cloning, and grew without fibronectin pre-coating of the dish. Optimal growth for the RL-65 clonal line was found to require only pins, hTF, eth, Peth, Sel, HC, FK (7F) and BPE at the concentrations shown in Table 1. The remaining factors, progesterone, T3, bovine lipoprotein and EGF, showed no further growth stimulation in the presence of the optimal 7F and BPE supplements and were omitted. RL-65 exhibited a doubling time of 17 hours, and had a 50–100 fold increase in $^3$H thymidine incorporation in this medium (FIG. 1). Neither 7F, in the absence of bovine pituitary extract, nor pituitary extract alone could stimulate cell division to the same extent as the combination. Each of the 8 components used in the optimized medium has proved to be essential to achieving an optimal doubling time, BPE being the most crucial. 10% Fetal bovine serum alone did not stimulate to optimal growth levels. This may be due less to inhibitory substances in serum than to a lack of essential growth factors, either absent in serum, or not provided in the necessary concentration. In the presence of those factors required for growth, serum was not inhibitory (FIG. 2).

Figure 3:
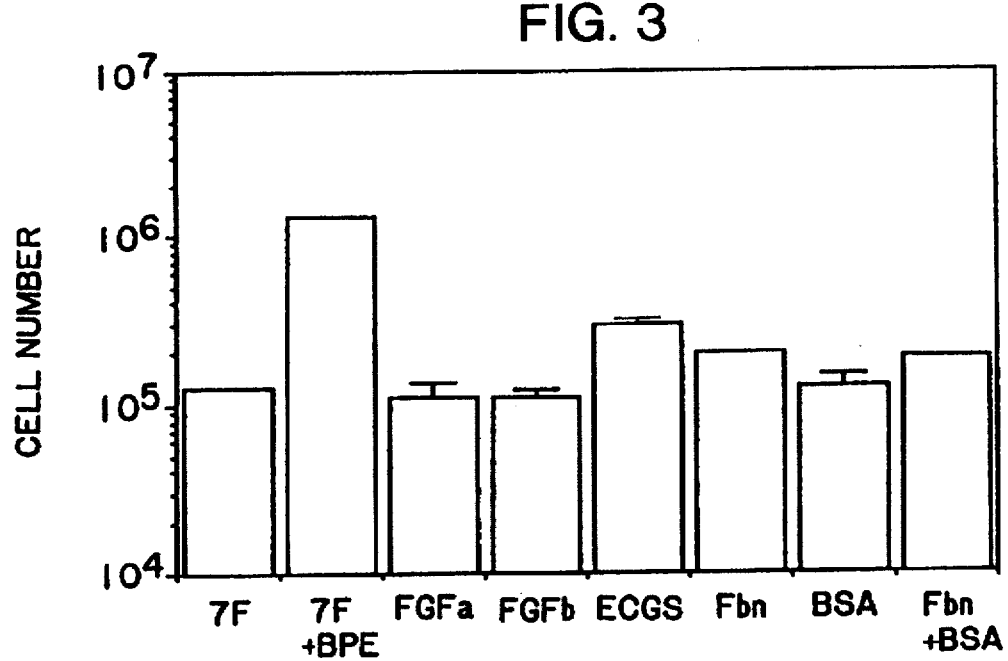
FIG. 3 Effect of FGF acidic (FGFa, 5 ng/ml), FGF basic (FGFb, 5 ng/ml), endothelial cell growth supplement (ECGS, 100 mg/ml), fibronectin (Fbn 30 μg/21 cm$^2$), and bovine serum albumin (BSA, 15 mg/ml).
Figure 4A:
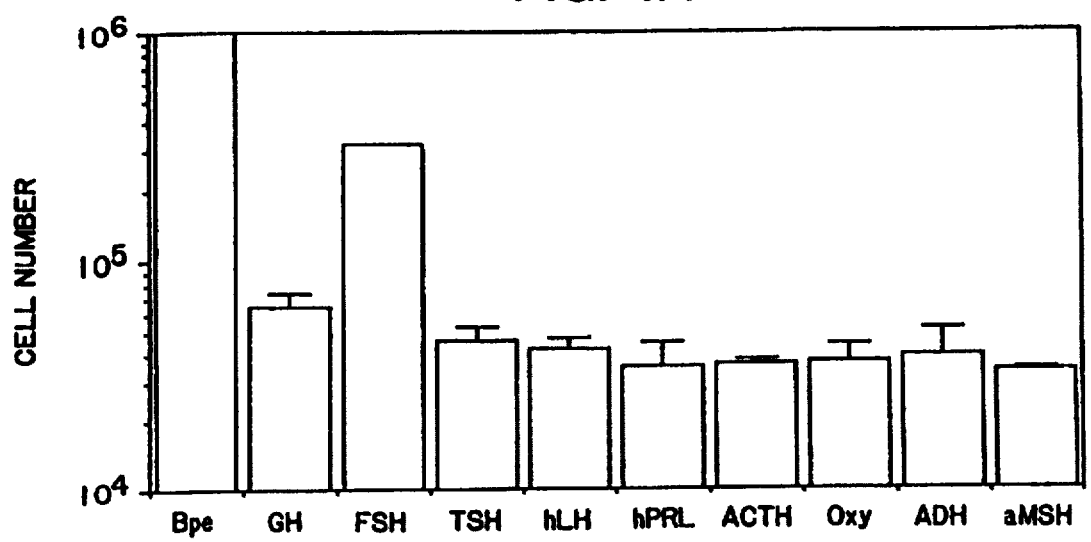
FIG. 4A–B. A. Effect of pituitary growth factors on growth of RL-65. Each factor was added in the presence of 7F and compared to 7F supplemented with BPE or 7F alone (±sem). A. GH, 1 mg/ml; FSH, TSH, 10 mg/ml; hLH, hPRL, 5 ng/ml; ACTH, Oxy, ADH, αMSH, B. βMSH, 10 ng/ml, β-lipotropin fragments, β, α, γ endorphin, 100 ng/ml, FGF, 3 ng/ml.
Figure 4B:
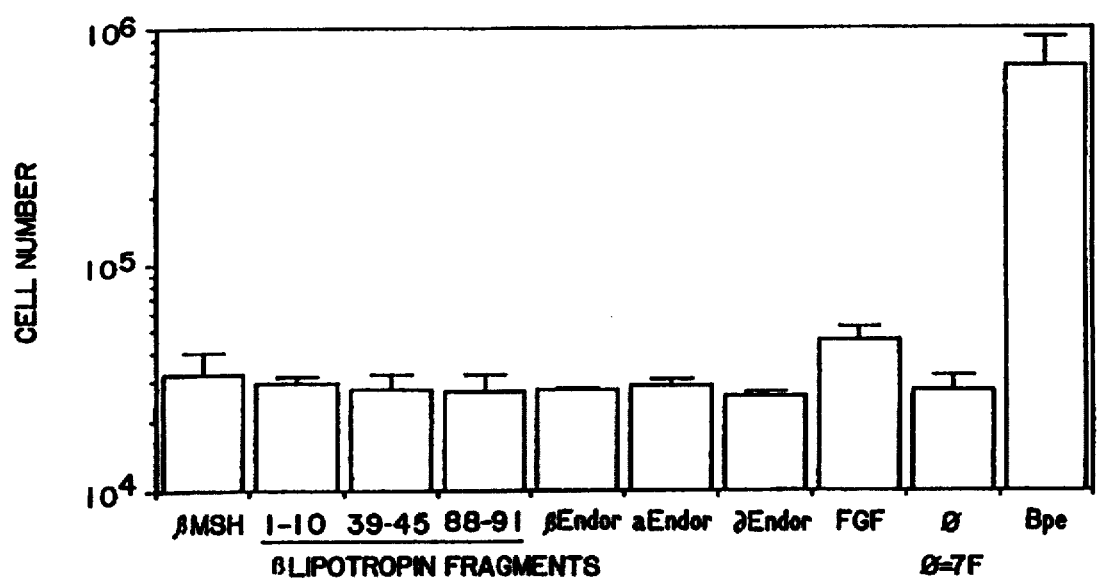

BSA, fibronectin, endothelial cell growth supplement (ECGS) and fibroblast growth factor (FGF), all present in pituitary extract, could not alone, or in combination, account for the response to BPE (FIG. 3). Initial screening of all known and commercially available pituitary factors, at varying concentrations, alone and in combination, demonstrated no stimulation over control (FIG. 4). While a crude preparation of FSH appeared to stimulate growth (FIG. 4), 2 different more highly purified preparations had no growth stimulatory activity, suggesting the growth promoting activity in the crude preparation was due to a non-FSH contaminant.

Nutrient and Hormone Interactions

Serum-free media was prepared by supplementing F12/DME with a mixture of hormones, growth factors and trace elements. F12/DME, mixed 1:1, was initially selected as the basal medium because of its widespread use in supporting the growth of a large variety of mammalian cells. In FIG. 5, the media composition was based on published reports: HTE, hamster tracheal epithelial (Wu et al., J. Cell Physiol. 125:167–181 [1985]); NHBE, normal human bronchial epithelial (Lechner et al., In Vitro 18:633–642 [1982]); HuTB, human tracheobronchial (Chopra et al., J. Cell Physiol. 130:173–181 [1987]). Basal media formulations previously shown to be optimal for hamster and human tracheal epithelial cells, and human bronchial epithelial cells were either inhibitory or not optimal for the growth of RL-65 (FIG. 5). These included some of the MCDB media (MCDB 151, 152, 153, 301 and 302) originally developed in Ham's lab for the growth of human keratinocytes (Tsao et al., J. Cell Physiol. 110219–229 [1982]), and modified by other labs for the growth of airway epithelial cells. Other cell types of the lung, such as the epithelial mink lung cell line, were unable to grow or survive in the optimized RL-65 medium.

The addition of 0.051 µM retinoic acid further increased cell number in the presence, but not in the absence of BPE.

EXAMPLE 2

CHARACTERIZATION OF CELL LINE RL-65

Indirect Immunofluorescence.

Cells were grown to near confluency on 12 mm glass coverslips. The coverslips were moved to fresh serum-free F12/DME and paraformaldehyde added to a final concentration of 2%. After 20' the coverslips were washed with phosphate buffered saline (PBS), and placed in 0.1M Glycine for an additional 20'. After washing 2× in PBS, 1% Triton-X 100 was added and left on for 6'. The coverslips were then washed 2× with PBS and exposed to the first antibody (diluted 1:25) for 30' at 37° C. After rinsing 4× in PBS (5'/rinse), the second antibody (1:10) was added and the above procedure was repeated. The coverslips were then drained, air dried, mounted in Aquamount, and examined with a Nikon Microphot FX epiflourescence microscope.

Electron Microscopy

Near-confluent cultures of primary lung cells or the established RL-65 line were prepared for electron microscopy by washing the cells with serum-free F12/DME, diluting the medium 1:1 with 2.5% gluteraldehyde in 0.2M phosphate buffer (pH 7.2), then fixing overnight in 2.5% gluteraldehyde. Alternatively, cells were grown on collagen coated Transwell membrane inserts (Costar) in 6-well trays, and fixed as above. Cultures were postfixed in 1% buffered $O_5O_4$, dehydrated in alcohol, and embedded in Polybed (Polysciences, Inc.). Sections cut on a Reichart OmU3 ultratome were stained in 3% aqueous uranyl acetate at 50° C. for 1 hr. and examined with a Phillips 300 microscope.

Quantitative Assay of Growth. Cells were seeded into 60 mm dishes and counted on day 5. Cells were dispersed by trypsinization and counted with a Coulter counter (Model ZF). Viability was determined by the ethidium bromide/acridine orange method (Parks et al., Proc. Natl. Acad. Sci. U.S.A. 76:1962–1966 [1979]). Thymidine incorporation studies were done at 24, 48, and 72 hours after plating. Cultures which were seeded at $5 \times 10^4$ cells/60 mm dish (4 ml/dish) were pulsed for 3 hrs. with 1 uCi/ml $^3$H thymidine. Dishes were rinsed 1× in serum-free F12/DME, then rinsed 2× in 5% trichloroacetic acid (TCA). One ml of 0.1N NaOH was added to each dish and after 15 minutes 0.5 ml from each dish was transferred to a 7.5 ml mini-vial. To each vial was added 3.5 ml of scintillation fluid and 200 ml of 40% acetic acid. Vials were counted for 1 minute each in a Beckman 3800 counter. This assay can be appropriately scaled for use in smaller or larger culture dishes as needed.

Ultrastructure.

The most prominent feature of the primary cultures grown in 11F supplemented with BPE are expanded ER and numerous microvilli. Additionally, there are many microfilaments, connected together by desmosomes on cellular processes. Cells grown in the presence of retinoic acid had a markedly different morphology exhibiting more densely packed colonies and a complete absence of cornification or keratinization.

In the presence of retinoic acid (0.05 mM), the epithelium resembles a low non-keratinized transitional or squamous epithelium. As in a typical epithelium of this type, basal cells are cuboidal in shape and apical cells more squamous. The absence of retinoic acid in the culture medium totally alters the morphological appearance of the cultures. Cells grown on membrane inserts exhibit an epithelium which is very obviously keratinized. In cultures which have been grown long enough to be a few cells deep, the apical cells (distal to the membrane) become flattened, whereas the basal cells are cuboidal. Desmosomes are prominent as are numerous epidimal filaments. Filaments are observed throughout the epithelium, even in the basal cells.

When cultures in the absence of retinoic acid are allowed to grow longer, the epithelium becomes more stratified and so highly keratinized that the epical cells die. Sections cut parallel to the filter membrane reveal elaborate networks of epidermal filaments. Viewed at high magnification, the organelles of this highly differentiated, keratinized, stratified epithelium are seen to be highly developed. Desmosomes, indistinguishable from normal skin, are associated with typical monofilaments. Large granules, similar to keratinophylan granules are also observed in these cells, especially in cells near the apical surface of the epithelium. Epidermal filaments are particularly well developed in these cells. In sections cut parallel to the filter membrane, they appear in semiregular patterns of swirls and circles.

Phenotype of RL-65.

The primary and secondary lung cultures, as well as the established cell line RL-65, grown in the absence of retinoic acid, exhibit characteristics typical of epithelial cells. The cells were found to contain alpha keratin, as determined by indirect immunoflourescence, as well as other cytoskeletal proteins, actin, desrain, vimentin and tubulin. In addition, the cells reacted positively with antisera against the rat cell attachment proteins fibronectin and laminin. The nitroblue tetrazolium dye reduction in the presence of NADPH is present in RL-65. This is specific for alveolar macrophages, alveolar type II cells, and non-ciliated bronchiolar epithelial (Clara) cells. RL-65 secrets IGF-I in the presence of retinoic acid; exhibits enkephalinase-like activity; exhibits transforming growth factor-beta (TGF-β) activity and binding; has acetylated LDL metabolism, produces endothelin and has abundant smooth endoplasmic reticulum.

Confirmation of Clara Cell Phenotype for RL-65

Figure 6A:
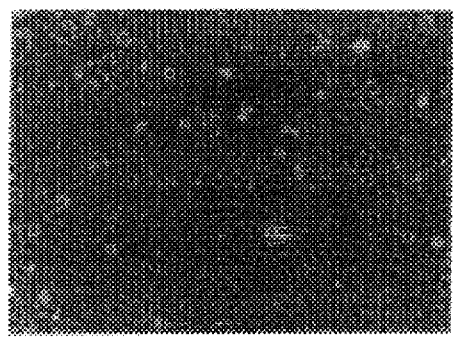
FIG. 6A–C. Photographs of cellular morphology: A) RL-65 in culture; B) rat bronchiole primary cells in culture; C) mouse primary Clara cells in culture.
Figure 6B:
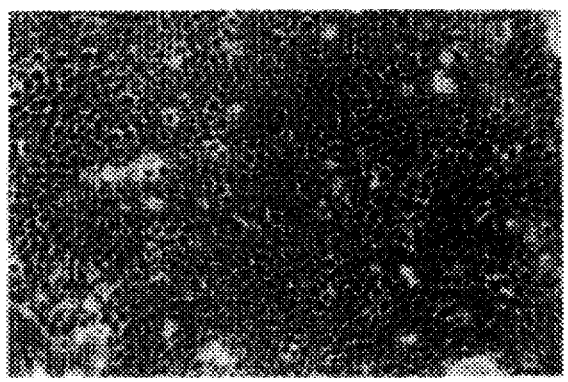
Figure 6C:
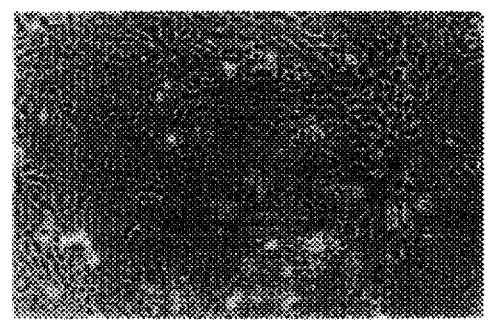

The repeated isolation of a Clara cell-like phenotype has been accomplished using the isolation methods disclosed. This cell type has been isolated from rat peripheral lung 7 times, from dissected rat bronchioles 2 times and from isolated mouse Clara cell populations (80% pure) 2 times. Characterization, in terms of nitroblue tetrazolium (NBT) dye reduction in the presence of NADPH, PGE-2 and thromboxane systhesis, prostaglandin synthetase and P-450 reductase has been consistent in the three cell types. The cells look morphologically the same in culture as illustrated in the FIG. 6a–c. FIG. 6a shows RL-65 in culture; 6b shows rat bronchilole primary cell culture; and, 6c shows mouse Clara cells in primary cell culture. Morphologically all three cells appear the same in culture. The combination of morphological appearance in culture and the presence of specific markers supports the characterization of the RL-65 as being of Clara-cell origin, or as a precursor of this cell type.

The properties of RL-65 used to identify them as Clara cells may be summarized as follows:

1. NBT dye reduction in the presence of NADPh.
2. Cytochromes P-4501 and P-450$_{II}$
3. Cytochrome P-450 reductase
4. Prostaglandin synthetase
5. Thromboxane
6. Abundant smooth endoplasmic reticulum
7. Actively secretory

EXAMPLE 3

LUNG CELL ASSAY SYSTEM

Mammalian epithelial lung cells produced by the method of Example 1 may be used to assay for the presence of growth promoting substances. The cell is used as a biological indicator with the growth of the lung cell serving as the assay for the presence of the growth promoting substance during the purification process. The lung cell may be used to assay fractions from any commonly practiced purification procedures, such as ion exchange chromatography, affinity chromatography, isoelectric focusing, gel exclusion chromatography, centrifugation, electrophoresis and other methods which separate various molecules on the basis of their physical or chemical properties. Specific methods suitable for separating the growth promoting substances are more fully described in volume 1 or 2, Current Protocols in Molecular Biology, Wiley Interscience (1989), Chapter 10, Analysis of Protein, specifically describes preferred methods for separating protein.

One type of growth promoting factor which may be purified by the lung cells of the present invention is the pituitary extract factor which promotes growth of the epithelial lung cells of Example 1. For example, if the lung cells are rat lung cells and the pituitary extract is bovine, the following illustrates the procedures to be used. The rat lung cell utilized is designated RL-65.

I. METHODS

A. 108S Pituitary Extract Preparation

Bovine pituitary extract (BPE) is made by homogenizing 105 g mixed sex bovine pituitaries in 250 ml cold 0.15M NaCl for 10 minutes in a blender. The homogenate is then transferred to a cold beaker and stirred for 90 minutes at 4° C. Next it is centrifuged at 4° C. for 40 minutes at 9800×g. The pellet is discarded and the supernatant is aliquoted into 50 ml polypropylene tubes and at this point can be stored at −20° C. Aliquots are filtered through a 0.8 m filter and then subjected to ultracentrifugation at 108,000×g for 3 hours or about 100,000×gravity for about 3 hours. The supernatant is carefully decanted, filter sterilized through a 0.22 m filter, and stored in 5 ml polypropylene "snap-cap" tubes at −70° C.

B. Bioassay

1. Cell Number

Cells are plated in 60 mm dishes (4 ml/dish) at a seed density of 5×10$^4$ cells/dish and counted on day 5 using a Coulter Counter ZF. Alternatively, cells are plated in 35 mm wells (6-well trays, 2 ml/well) at a seed density of 2.5×10$^4$ cells/well and counted on day 5.

2. Thymidine Incorporation

Thymidine incorporation studies were done at 24, 48 and 72 hours after plating. Cultures which were seeded at 5×10$^4$ cells/60 mm dish (4 ml/dish) or at 2.5×10$^4$/well (6-well tray, 2 ml/well) were pulsed for 3 hours with 1 uCi/ml $^3$H thymidine. Dishes were rinsed 1× in serum-free F12/DME, then rinsed 2× in 5% trichloroacetic acid (TCA). One ml of 0.1N NaOH was added to each dish and after 15 minutes 0.5 ml from each dish was transferred to a 7.5 ml mini-vial. To each vial was added 3.5 ml of scintillation fluid and 200 μl of 40% acetic acid. Vials were counted for 1 minute each in a Beckman 3800 counter.

II. PURIFICATION SCHEME

Purification of Bovine Pituitary Extract (108S)

| Mitogenic Activity on RL-65 Rat Lung Cells | Recovery % Bioactivity | Recovery % Protein Content |
|---|---|---|
| Gel filtration, BioGel P-300 | 20% | 40% |
| Affinity chrom.: anti-BSA | 100% | 70% |
| Affinity chrom.: Heparin-Seph | 100% | 95% |
| Affinity chrom.: Con A-Seph | 100% | 95% |
| Ion Exchange: HTP | 56% | 5–10% |
| Expected purification of 108S on combined HTP/anti-BSA column is 50–100 fold | 56% | 0.5% |

A. P-300 gel filtration. To concentrate on collecting fractions in the 50–100 Kd range, where mitogenic activity exists.

B. Heparin-sepharose and conA column to remove growth factors and attached proteins.

C. aBSA IgG column. To remove albumin and have a mitogenic eluate which can be further purified by use of HPLC.

D. Hydroxylapatite or HPLC.

Variations of the above scheme may be developed by substituting or adding other types of chromatography and by varying the ionic strength and pH of the solvent.

EXAMPLE 4

RECOMBINANT PRODUCTION OF HUMAN LUNG SURFACTANT IN LUNG CELL CULTURE

The cell line RL-65 was transformed by a recombinant expression vector to produce human lung surfactant protein C (SPC). The DNA encoding SPC was prepared according to the procedures previously described and SPC was expressed as previously by recombinant methods using published necleotide and amino acid sequences (Glasser, et al., Proc. Natl. Acad. Sci. U.S.A. 84:4007 [1987]; Jacobs, et al., J. Biol. Chem 262:9898 [1987]; Floros, et al., J. Biol Chem. 261:9029 [1986]; White, et al., Nature 317:361 [1985]; Glasser, et. al., J. Biol. Chem 263:9 [1988]; Glasser et. al., J. Biol. Chem. 263:10326 [1988]; and Jobe et al., Am. Rev. Resp. Dis. 136:1032 [1987]). The plasmid pdH135 containing an SV40 promoter in expression plasmid pSVI was transfected into RL-65 using lipofectin from BRL, Inc. The DNA sequence of plasmid pSVI is shown in FIG. 7. The plasmid pSVI was constructed from pRK5 (described in EP 307,247 where the pCIS2.8c28D starting plasmid is described in EP 278,776 published Aug. 17, 1988) and pE348DHFRUC (Vannice and Levinson, J. Virology, 62:1305–1313). The cell were plated in either 12-well trays at 5×10⁵ cells/well or in 60 mm dishes at 1×10⁶ cells/dish in 7F media without bovine pituitary extract.

In 60 mm dishes the following concentrations of reagents were used:

10 μl dh135 at a concentration of 1.5 μg/μl 4.0 μl dhfr at a concentration of 430 ng/μl.

40 μl Lipofectin

106 μl water

The above is added to each 60 mm plate containing 5 ml medium+7F+BPE,

In 12-well trays the following concentration of reagents were used:

36 μl dh135 at a concentration of 1.5 μg/μl

13 μl dhfr at a concentration of 430 ng/μl 158.4 μl Lipofectin

288 μl water

A total of 33 μl per well was used in each 1.0 ml well.

The dishes or trays were incubated for 72 hours after which they were washed with serum-free medium F12/DME and 7F medium was added back in GHT-F12/DME. The cells were titrated with methyltrexate, with optimum at 50–100 mM. The cells were maintained in this medium and periodically assayed for SPC by spotting onto nitrocellulose, incubating in the presence of SPC antibody overnight and visualizing with an alkaline phosphatase immunostaining technique using antibody specific for SPC. The nitrocellulose membrane was placed in a 96-well vacuum manifold (Schleicher and Schuel) and 200 ml of conditioned medium added per well. Vacuum was applied to the manifold and the conditioned medium was drawn through the nitrocellulose membrane. The nitrocellulose membrane was air dried and placed in 0.5% Tween-20 for blocking, then incubated in anti-SPC rabbit antibody (1:500) overnight at 4° C. The nitrocellulose membrane was washed in 0.05% tween-20 three times, then incubated in 1% goat serum for 15 min at room temperature(RT). Goat anti-rabbit IgG-alkaline phosphatase (1:1000) was added and incubated at RT for 40 min. The membrane was washed at RT in 0.05% NP-40 for 10 min., in 0.05% Tween-20 for 10 min. and CHES buffer for 10 min. The membrane was then assayed for alkaline phosphatase using standard procedures.

The amount of surfactant produced by the cells and released into 10-day conditioned medium was determined by growing the transformed RL-65 cells for 10 days and removing 200 ml of conditioned medium, spotting it on nitrocellulose as described above. One well of a 24 well tray, clone 5, produced a spot on nitrocellulose indicating the conditioned media contained 1.1 mg/ml human lung surfactant C.

---

We claim:

1. A method for the assay of a growth promoting substance comprising:

(a) incubating an established normal mammalian bronchial or bronchiolar epithelial lung cell line in a medium containing said growth promoting substance; and (b) quantifying a growth indicating property of said bronchial or bronchiolar epithelial lung cell line, wherein said bronchial or bronchiolar epithelial lung cell line is derived from lung cells isolated by incubating the lung cells in serum free medium 11F, wherein said bronchial or bronchiolar epithelial lung cell line is not established by transformation with viral DNA, and wherein said bronchial or bronchiolar epithelial lung cell line is able to be maintained for multiple passages in the absence of serum without undergoing senescence.

2. The method according to claim 1 wherein said lung cell line is a rat lung cell line.

3. The method according to claim 1 wherein said lung cell line is a human lung cell line.

4. The method according to claim 2 wherein said rat lung cell line is RL-65, ATCC CRL 10354.

5. The method according to claim 1 wherein said growth promoting substance is found in a pituitary extract.

6. The method according to claim 1 wherein said growth indicating property is cell number.

7. The method according to claim 1 wherein said growth indicating property is DNA synthesis.

8. The method according to claim 7 wherein said DNA synthesis is indicated by the incorporation of a radioactive nucleotide.

9. The method according to claim 8 wherein said radioactive nucleotide is tritiated thymidine.

10. The method according to claim 5 wherein said pituitary extract is a soluble extract remaining after ultracentrifugation at about 100,000×gravity for about 3 hours.

11. The method of claim 1, wherein the cell line is a non-ciliated bronchiolar epithelial Clara cell line.

* * * * *

UNITED STATES PATENT AND TRADEMARK OFFICE
CERTIFICATE OF CORRECTION

PATENT NO.      :   5,736,345

DATED           :   April 7, 1998

INVENTOR(S)     :   Mather et al.

It is certified that error appears in the above-identified patent and that said Letters Patent is hereby corrected as shown below:

Column 19, Claim 1, line 30, delete "vital" and insert  --viral--.

Signed and Sealed this

Thirtieth Day of June, 1998

Attest:

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 664 bases
        ( B ) TYPE: nucleic acid
        ( C ) STRANDEDNESS: double
        ( D ) TOPOLOGY: linear ( x i ) SEQUENCE DESCRIPTION: SEQ ID NO:1:

```
TTCGAGCTCG  CCCGACATTG  ATTATTGACT  AGAGTCGACA  GCTGTGGAAT   50

GTGTGTCAGT  TAGGGTGTGG  AAAGTCCCCA  GGCTCCCCAG  CAGGCAGAAG  100

TATGCAAAGC  ATGCATCTCA  ATTAGTCAGC  AACCAGGTGT  GGAAAGTCCC  150

CAGGCTCCCC  AGCAGGCAGA  AGTATGCAAA  GCATGCATCT  CAATTAGTCA  200

GCAACCATAG  TCCCGCCCCT  AACTCCGCCC  ATCCCGCCCC  TAACTCCGCC  250

CAGTTCCGCC  CATTCTCCGC  CCCATGGCTG  ACTAATTTTT  TTTATTTATG  300
```

```
CAGAGGCCGA GGCCGCCTCG GCCTCTGAGC TATTCCAGAA GTAGTGAGGA 350

GGCTTTTTTG GAGGCCTAGG CTTTTGCAAA AAGCTTATCG GGCCGGGAAC 400

GGTGCATTGG AACGCGGATT CCCCGTGCCA AGAGTGACGT AAGTACCGCC 450

TATAGAGTCT ATAGGCCCAC CCCCTTGGCT TCGTTAGAAC GCGGCTACAA 500

TTAATACATA ACCTTATGTA TCATACACAT ACGATTTAGG TGACACTATA 550

GAATAACATC CACTTTGCCT TTCTCTCCAC AGGTGTCCAC TCCCAGGTCC 600

AACTGCACCT CGGTTCTAAG CTTGGGCTGC AGGTCGCCGT GAATTTAAGG 650

GACGCTGTGA AGCA 664
```